United States Patent
Gunaratnam et al.

(10) Patent No.: US 6,439,230 B1
(45) Date of Patent: Aug. 27, 2002

(54) MASK WITH RECESS INCLUDING AT LEAST ONE MASK PORT

(75) Inventors: Michael K Gunaratnam, Marsfield; Amal Amarasinghe, West Pennant Hills, both of (AU)

(73) Assignee: ResMed Limited, New South Wales (AU)

(*) Notice: Subject to any disclaimer, the term of this patent is extended or adjusted under 35 U.S.C. 154(b) by 0 days.

(21) Appl. No.: 09/504,234

(22) Filed: Feb. 15, 2000

Related U.S. Application Data

(63) Continuation-in-part of application No. 29/115,618, filed on Dec. 16, 1999, now Pat. No. Des. 443,355.

(30) Foreign Application Priority Data

Jun. 18, 1999 (AU) .................................................. 1916/99

(51) Int. Cl.⁷ .............................................. A61M 16/00
(52) U.S. Cl. ........................... 128/206.21; 128/204.18; 128/206.12; 128/205.25; 128/206.28; 128/207.18
(58) Field of Search ........................ 128/206.21, 206.12, 128/205.25, 206.15, 206.16, 206.28, 206.26, 203.22, 204.18, 206.18, 207.13, 207.18, 203.29, 204.12

(56) References Cited

U.S. PATENT DOCUMENTS

| | | | | |
|---|---|---|---|---|
| 718,785 | A | * 1/1903 | McNary | 128/207.18 |
| 4,231,363 | A | 11/1980 | Grimes | |
| 4,807,617 | A | * 2/1989 | Nesti | 128/203.29 |
| 4,944,310 | A | * 7/1990 | Sullivan | 128/205.25 |
| 5,233,978 | A | 8/1993 | Callaway et al. | |
| 5,311,862 | A | * 5/1994 | Blasdell et al. | 128/205.19 |
| 5,724,965 | A | 3/1998 | Handke et al. | |
| 5,918,598 | A | 7/1999 | Belfer et al. | |
| 6,196,223 | B1 | * 3/2001 | Belfer et al. | 128/205.25 |

FOREIGN PATENT DOCUMENTS

| | | |
|---|---|---|
| FR | 2766723 | 2/1999 |
| GB | 649689 | 1/1951 |

* cited by examiner

Primary Examiner—Aaron J. Lewis
Assistant Examiner—Mital Patel
(74) Attorney, Agent, or Firm—Pillsbury Winthrop LLP

(57) ABSTRACT

Mask ports 180 for attaching supplemental oxygen tubes 510 or measurement devices to a respiratory mask are downwardly directed and recessed into the base 110 of the mask frame 100. The ports may comprise a pair of downwardly extending tubular spigots 185 each housed in a respective recess 190 in the base 110, with a shallow bridging recess 290 therebetween for receiving a bridging piece 300 of a closure cap 280.

15 Claims, 4 Drawing Sheets

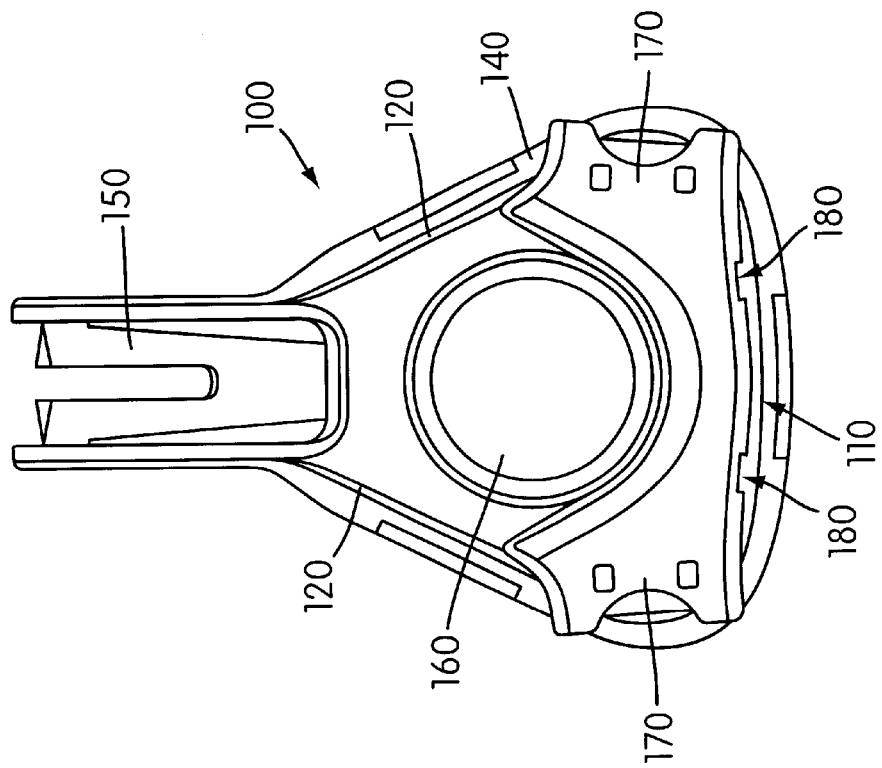
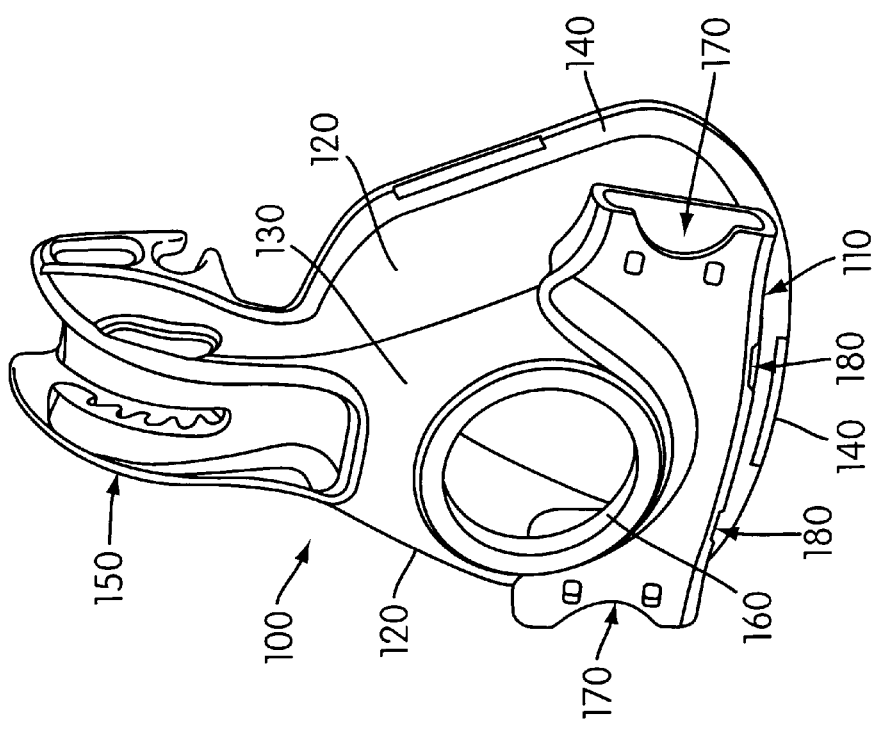

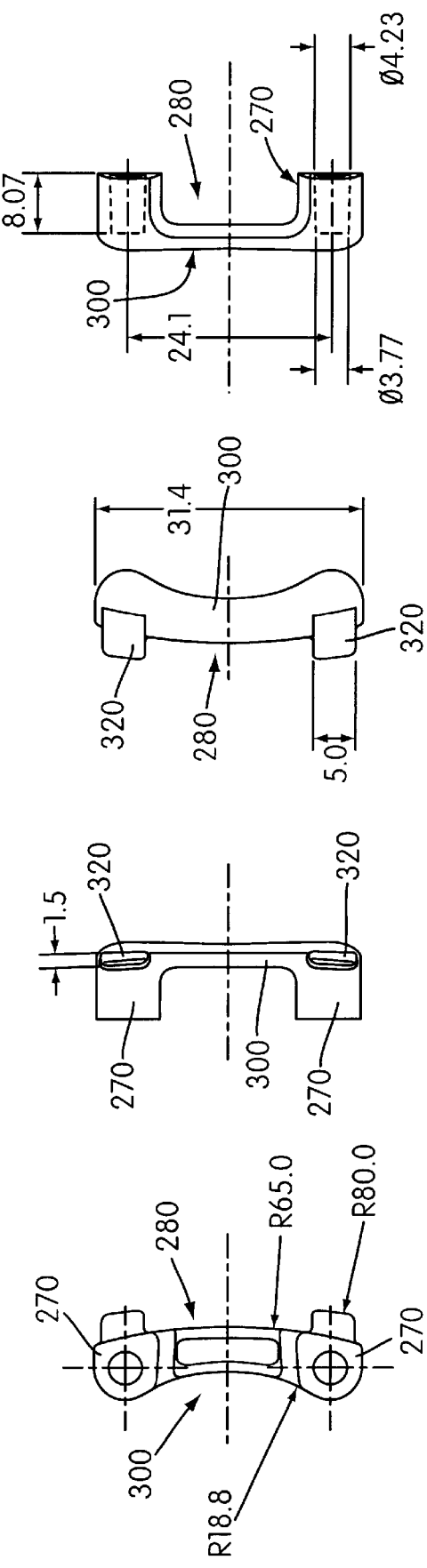

MASK WITH RECESS INCLUDING AT LEAST ONE MASK PORT

This application is a continuation-in-part of Ser. No. 29/115,618 filed Dec. 16, 1999 now U.S. Pat. No. D,443,355.

FIELD OF THE INVENTION

The invention relates to masks suitable for the delivery of breathable gases to a patient for the treatment of sleep disordered breathing (SDB), and to mask ports for such masks.

BACKGROUND OF THE INVENTION

Respiratory masks used in the treatment of SDB may comprise a nasal mask, designed to fit over a patient's nose, or a full face mask designed to fit over the nose and mouth of the patient. In both cases, the mask is held in position by headgear.

The mask generally comprises a relatively rigid shell, termed a frame, which defines a rearwardly opening cavity covering the patient's nose and/or mouth and a soft portion, termed a cushion, which spaces the frame away from the face for comfortable contact.

The air or other breathable gas is supplied by a blower and passed along a flexible conduit to the mask. The conduit is typically of relatively large bore, for example approximately 2 cm diameter, with the mask frame having a gas inlet of comparable diameter.

In addition to the gas inlet, the mask may also have $CO_2$ washout vents and one or more small diameter ports through which supplemental oxygen may be introduced or measurements made. The ports typically comprise a pair of cylindrical connectors moulded into the mask frame, usually projecting forward from the front surface of the frame. The mask ports typically also include a cap which prevents leakage of air from the mask when the port is not in use.

Depending on the part construction and the relative diameters of the port and the tubing which supplies supplemental oxygen, the port may function as a male or a female connector. The Mirage® nasal mask (ResMed Ltd.) is a generally triangular mask with a gas inlet tube extending upwards from its apex. The two ports of that mask are located in the front of the gas inlet tube just above the patient's eye level, between a pair of shield projections. A single cap of silicone rubber covers both ports, and has tabs at either end to facilitate removal by pulling on the tabs in a direction away from patient's face.

There is a need for ports which are conveniently located on the mask, which are protected from accidental breakage and which do not foul tubing. There is a need for a corresponding port cap which is sufficiently large so as to be easy to handle and which is not so small as to be easily lost.

SUMMARY OF THE INVENTION

The present invention provides a mask Fame for a respiratory mask, said mask frame defining a mask cavity adapted for communication with a patient's airways and including a gas inlet adapted for connection to a supply of breathable gas, further including a recess in a lower portion of the mask frame, at least one mask port comprising a downwardly extending tubular spigot located in said recess, said spigot having a bore communicating with the mask cavity via a port aperture in the mask frame.

The cap is preferably constructed from a single piece of silicone or other elastomeric material with tabs preferably to the front of the mask when positioned on the ports. Preferably the base of the cap is flush with the base of the mask. Preferably, to remove the cap, the tabs are pulled in a downwards motion, relative to the front of the mask A further form of the invention provides a mask frame for a respiratory mask, said mask frame defining a mask cavity adapted for communication with a patient's airways including a gas inlet adapted for connection to a supply of breathable gas, further including at least one downwardly opening port located in a lower portion of the mask frame and communicating with the mask cavity.

BRIEF DESCRIPTION OF THE DRAWINGS

Further embodiments of the invention will now be described with reference to the accompanying drawings, in which:

FIG. 1 shows a side perspective view of a mask frame.

FIG. 2 shows a front view of the mask frame of FIG. 1.

FIG. 3b shows a section B—B from FIG. 3a.

FIG. 3c shows a section C—C from FIG. 3a.

FIG. 4a shows a perspective view of the port cap.

FIG. 4b shows an end view of the port cap.

FIG. 4c shows a top view of the port cap.

FIG. 4d shows a front view of the port cap.

FIG. 4e shows a bottom view of the port cap.

FIG. 4f shows a rear view of the port cap.

In FIGS. 4a to 4f approximate dimensions are indicated in mm.

DETAILED DESCRIPTION OF THE INVENTION

Figure 3A:
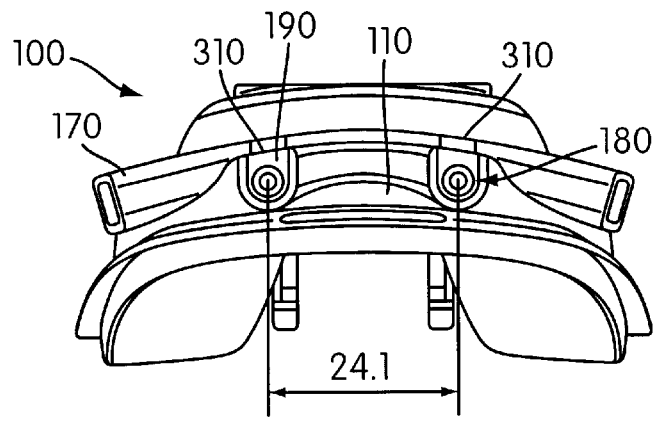
FIG. 3a shows a bottom view of the mask frame of FIG. 1.

FIGS. 1 and 2 illustrate a mask frame 100 for a nasal mask, formed as a moulded shell of polycarbonate or similar rigid material, which acts as a body onto which the other components of the mask are attached. A suitable material for the mask frame is Makrolon 2458 polycarbonate from Bayer.

The fame 100 is generally triangular in front view, having a base 110, a pair of inclined side walls 120 extending towards an apex and a front wall 130. The frame defines a mask cavity covering the patient's nose, and is open at its rear. A rim 140 at the rear edge of the base 110 and side walls 120 approximates the contours of the patient's face and is adapted for attachment of a soft mask cushion (not shown) to pace the frame away from the patient's face for sealing and comfort The apex of the frame has an extension 150 for attachment of a forehead support (not shown).

In the illustrated mask frame, a gas inlet aperture 160 is formed in the front wall 130, for connection of a gas supply conduit or similar, which may include an elbow connector (not shown) pivotably connected to the frame. In other forms of mask, the gas inlet aperture may be formed at the apex of the frame.

The mask frame further includes lower headgear connection points 170 for attachment to the headgear which holds the mask in place on the patient's face. Upper headgear connection points may be formed in tie forehead support (not shown).

With reference to FIGS. 1 to 3a, it can be seen that the mask frame includes two ports 180, approximately 2.5 cm apart, located in recesses 190 in the base of the mask frame 100. These recesses are positioned in between the lower headgear strap connection points 170. The ports are positioned so that in use, oxygen or other breathable gas can be delivered close to the patient's nares.

Each port is formed as a tubular spigot 185 with an approximate external diameter of 4 mm and an approximate length of 1 cm. The spigot 185 forms the male connector onto which small bore tubing supplying, for example, oxygen, may be attached.

Figure 3B:
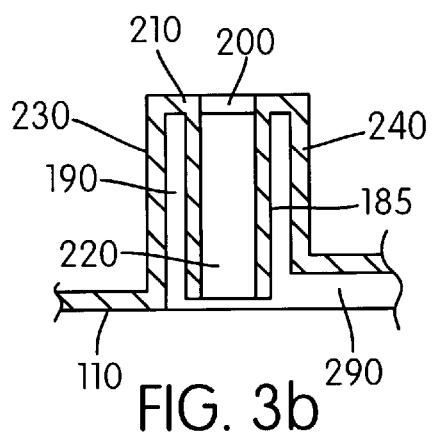
Figure 3C:
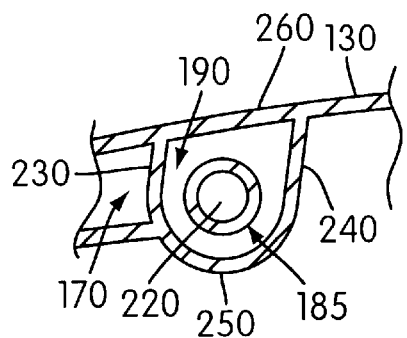

An elevational cross-section through the port is shown in FIG. 3b, and a lateral cross-section at FIG. 3c.

As best seen in FIGS. 3b and 3c, each recess 190 is approximately rectangular in elevation (FIG. 3a) and closed off from the mask cavity except for an aperture 200 extending through the recess upper wall 210 between the bore 220 of the spigot 185 and the mask cavity. The recess is bounded by the upper wall 210, side wall portions 230, 240 and a rear wall portion 250, and is open at its bottom end. A front wall 260 is formed as a continuation of the front wall 130 of the mask frame. The rear wall portion 250 and one or both side wall portions 230, 240 may be formed as a continuous curve.

These boundary walls 230, 240, 250, 260 of the recess are spaced from the spigot by a sufficient distance, for example at least 1 mm, to allow a small bore oxygen tube to be pushed onto the spigot, and also to allow the closure portion 270 of a cap 280 (FIGS. 4a to 4f) to be retained.

The base 110 of the mask also includes a shallow bridging recess 290 for receiving the bridge piece 300 joining the two closures 270 of the cap 280.

The bottom edge of the frame front wall 130 includes a pair of small notches 310 through which gripping tabs 320 of the cap extend, so that the tabs extend forward of the front wall for gripping by the user. Pulling downwards on the tab will remove the respective closures 270 from its spigot 185 to allow attachment of an oxygen tube or a tube leading to a measurement device.

The cap 280 is suitably formed of a relatively soft elastomeric material, such as Dow Silastic 94-595 HC silicone.

As can be seen in FIGS. 1 and 2, the above construction results in the bottom of the cap 280 being substantially flush with the base 110 of the Fame 100, providing a compact and aesthetically pleasing arrangement.

The asymmetric shape of the recessed chamber and corresponding shape of the cap 280 reduces the likelihood that the cap 280 will be incorrectly positioned back-to-front.

A further advantage of recessing the ports into the mask frame is that the dead volume of the frame is reduced. A further advantage of providing access from the bottom of the mask frame is that the likelihood of fouling the gas delivery conduit is reduced where a swivel connection is used to provide air from the flow generator.

Another advantage is that the loss of supplemental oxygen through the vent is reduced by positioning the port away from the main vent path.

In other embodiments, there may be one port, or there may be more than two ports. Furthermore, ports may have individual caps. Ports may be connected by way of a small bore tubing or in any other suitable manner to a manometer for measuring pressure in the mask cavity during the setting up of the device or during treatment of SDB. Alternatively, one or more ports may be used in conjunction wit transducers and control algorithms to control the operation of an automatically adjusting device.

In an alternative embodiment, a lager diameter cylinder is used for the port, hence the cylinder will function as a female connector with respect to the supplemental oxygen tubing.

In another embodiment, the spigots could extend within the mask frame to bring the oxygen supply closer to the nares.

Figure 5A:
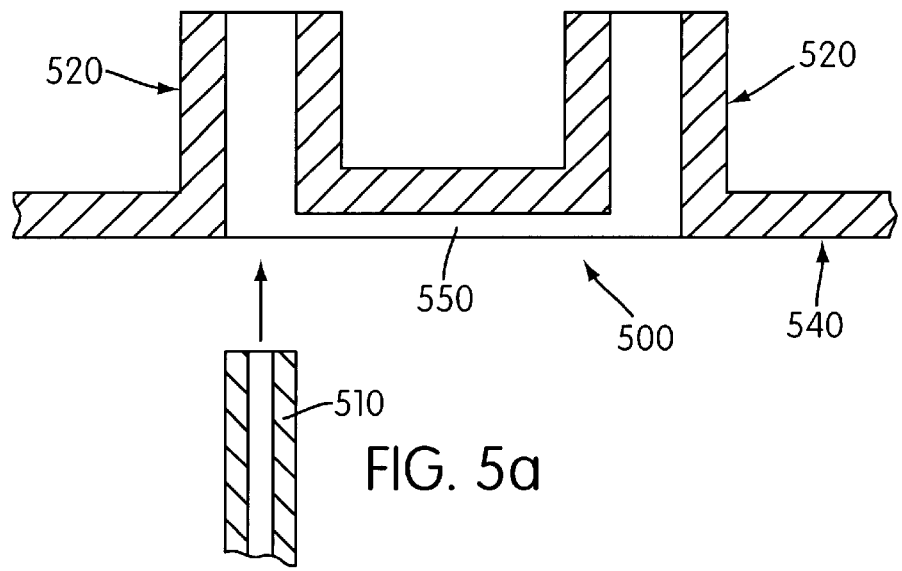
FIGS. 5a to 5c schematically illustrate an alternative embodiment of the invention.
Figure 5B:
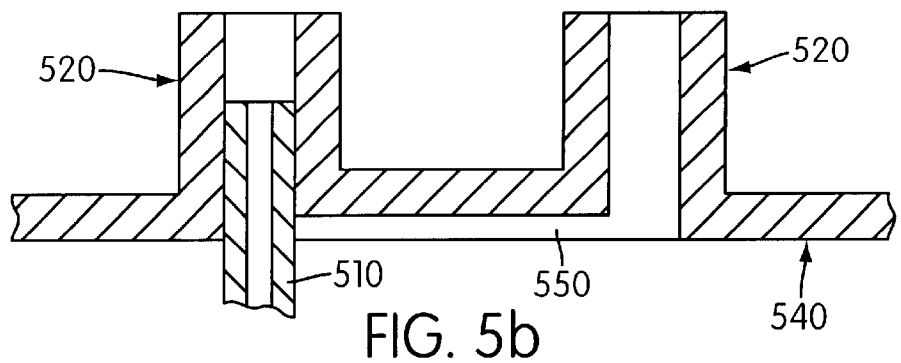
Figure 5C:
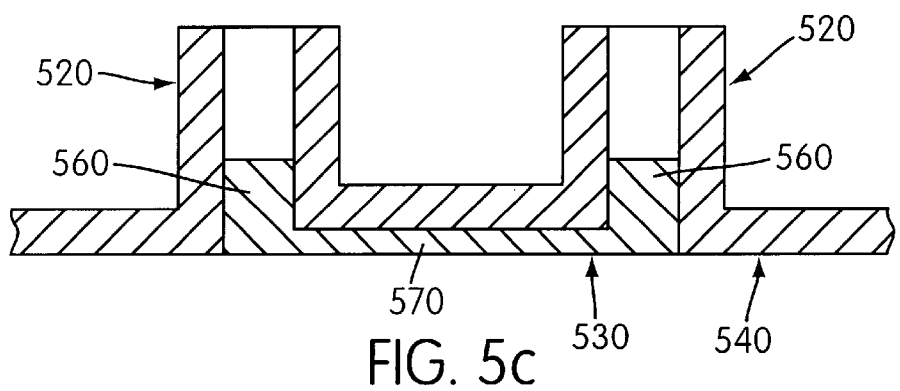

FIGS. 5a to 5c are schematic front elevational cross-sections of an alternative mask port arrangement 500 with, respectively, an oxygen delivery tube 510 being red into a port 520 (FIG. 5a), the delivery tube in position in the port (FIG. 5b), and the tube removed and a cap 530 inserted (FIG. 5c).

The position and orientation of the ports 520 is generally similar to that described above with reference to FIGS. 1 to 3c except that the ports 520 are formed as tubes extending upwards into the mask cavity, and open at their upper ends. In common with the previously described embodiment, the base 540 of the mask frame includes a pair of these recessed mask ports, joined by a shallow bridging recess 550.

As can be seen from FIGS. 5a and 5b, the port 520 acts as a female connector for insertion from below of a corresponding oxygen supply tube 510 having a diameter chosen for substantially sealing engagement in the port.

As shown in FIG. 5c, the configuration of the cap 530 is generally similar to that of FIGS. 4a to 4f, including a pair of closure portions 560 joined by a bridging portion 570, except that the closure portions for sealing the ports when not in use are preferably formed as solid plugs rather than as cup-shaped closures as in FIGS. 4a to 4f.

In another embodiment, the tabs 320 of the cap 280 are below the mask, rather than in front.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

What is claimed is:

1. A mask frame for a respiratory mask, said mask frame defining a mask cavity adapted for communication with a patient's airways and including a gas inlet adapted for connection to a supply of breathable gas, further including at least one recess in a lower portion of the mask frame extending inward into said mask cavity, at least one mask port comprising a tubular spigot located in said at least one recess and extending downward from said mask cavity within said at least one recess, said spigot having a bore communicating with the mask cavity via a port aperture in the mask frame, wherein an axial extent of said spigot is disposed substantially within said at least one recess.

2. A mask frame according to claim 1 wherein said at least one recess is bounded by at least an upper wall portion, opposed side wall portions and a rear wall portion and is open at a bottom end thereof, said wall portions being spaced from the spigot so as to allow a tube to be pushed over the spigot through said open bottom end of the at least one recess.

3. A mask frame according to claim 2 wherein said at least one recess is further bounded by a front wall formed as part of a front wall of the mask frame.

4. A mask frame according to claim 2 wherein said port aperture extends through said upper wall portion of said at least one recess.

5. A mask frame according to claim 2 wherein said gas inlet is located in said front wall of the mask frame, above said at least one recess.

6. A mask frame according to claim 1, said mask frame being generally triangular in front view and having a front wall, a base, an apex, and a pair of inclined side walls extending from respective opposed ends of the base to said apex, wherein said at least one recess is formed in said base.

7. A mask frame according to claim 6 wherein said at least one recess includes a pair of recesses each housing a respective mask port.

8. A mask frame according to claim 7 further including a removable port cap having a pair of closure portions each adapted to be pushed into a respective one of said pair of recesses to seal a respective one of said ports, and a bridge portion connecting said closure portions.

9. A mask frame according to claim 8 wherein said port cap further includes at least one gripping tab which extends, in use, forward of said front wall of the mask frame.

10. A mask frame according to claim 8 wherein, in use, a base of said port cap is substantially flush with said base of the mask frame.

11. A mask frame according to claim 8 wherein said base her includes a shallow bridging recess extending between said pair of recesses, for receiving said bridge portion of the port cap.

12. A mask Same according to claim 1 wherein said mask is a nasal mask, and wherein said at least one port is adapted to introduce oxygen to a position below the patient's nares.

13. A mask frame according to claim 1 further including a tube having an end adapted for insertion in said at least one recess such that an inner surface of said tube substantially seals against an outer surface of said spigot.

14. A mask frame according to claim 1 further including a tube having an end adapted for insertion in said at least one recess such that an outer surface of said tube substantially seals against an inner surface of said spigot.

15. A mask frame for a nasal respiratory mask, said mask frame defining a mask cavity adapted for communication with a patient's airways comprising:

at least one recess in a lower portion of the mask frame extending inward into said mask cavity, said at least one recess being bounded by at least an upper wall portion, opposed side wall portions, a rear wall portion and a front wall portion formed as part of a front wall of the mask frame and being open at a bottom end thereof;

wherein said mask frame is generally triangular in front view and has a front wall, a at base, an apex, and a pair of inclined side walls extending from respective opposed ends of the base to said apex, wherein said at least one recess is formed in said base;

a gas inlet adapted for connection to a supply of breathable gas, wherein said gas inlet is located in said front wall of the mask frame, above said at least one recess;

at least one mask port, for attachment to at least one tube leading to a measurement device, comprising a tubular spigot located in said at least one recess and extending downward from said upper wall portion within said at least one recess, said spigot having a bore communicating with the mask cavity via a port aperture in the mask frame extending through said upper wall portion of said at least one recess, wherein an axial extent of said spigot is disposed substantially within said at least one recess and said wall portions are spaced from said spigot so as to allow a tube to be pushed over the spigot through said open bottom end of said at least one recess; and a removable port cap having at least one closure portion adapted to be pushed into said at least one recess to cover the at least one mask port, wherein said port cap further includes at least one gripping tab which extends, in use, forward of said front wall of the mask frame, wherein, in use, a base of said port cap is substantially flush with said base of the mask frame.

\* \* \* \* \*

UNITED STATES PATENT AND TRADEMARK OFFICE
CERTIFICATE OF CORRECTION

PATENT NO.     : 6,439,230 B1
DATED          : August 27, 2002
INVENTOR(S)    : Gunaratnam et al.

It is certified that error appears in the above-identified patent and that said Letters Patent is hereby corrected as shown below:

<u>Title page,</u>
Item [30], should read:
-- [30]  Foreign Application Priority Data
June 18, 1999   (AU) ............................... PQ1040
June 18, 1999   (AU) ............................... 1916/99 --

Signed and Sealed this

Twentieth Day of May, 2003

JAMES E. ROGAN
*Director of the United States Patent and Trademark Office*